United States Patent [19]

Ishizuka et al.

[11] 4,241,057
[45] Dec. 23, 1980

[54] ANTIBIOTIC COMPOSITIONS

[75] Inventors: Kenzo Ishizuka, Amagasaki; Hiroshi Fujisawa, Toyonaka; Etsunosuke Noda, Yao, all of Japan

[73] Assignee: Takeda Chemical Industries, Ltd., Japan

[21] Appl. No.: 19,185

[22] Filed: Mar. 9, 1979

Related U.S. Application Data

[62] Division of Ser. No. 828,841, Aug. 29, 1977, Pat. No. 4,161,527.

[51] Int. Cl.³ ............................................. A61K 31/545
[52] U.S. Cl. ................................. 424/246; 206/524.8
[58] Field of Search ...................... 206/524.8; 424/246

[56] References Cited

FOREIGN PATENT DOCUMENTS 823861  6/1975  Belgium ................................... 424/246

*Primary Examiner*—Jerome D. Goldberg
*Attorney, Agent, or Firm*—Wenderoth, Lind & Ponack

[57] ABSTRACT

Solid antibiotic compositions containing 7β-[2-(2-imino-4-thiazolin-4-yl)acetamido]-3-{1-[2-(N,N-dimethylamino)-ethyl]-1H-tetrazol-5-yl}thiomethyl-3-cephem-4-carboxylic acid dihydrochloride or its hydrate and a pharmaceutically acceptable carbonic acid salt are rapidly converted into an injectable solutions by the addition of a solvent, and the injectable solution shows high antibacterial activity with less local reactions when injected.

7 Claims, No Drawings

ANTIBIOTIC COMPOSITIONS

This is a division, of application Ser. No. 828,841, filed Aug. 29, 1977 now U.S. Pat. No. 4,161,527, issued on July 17, 1979.

The present invention relates to solid antibiotic compositions containing 7β-[2-(2-imino-4-thiazolin-4-yl)-acetamido]-3-{1-[2-(N,N-dimethylamino)ethyl]-1H-tetrazol-5-yl}thiomethyl-3-cephem-4-carboxylic acid dihydrochloride or its hydrate as an effective ingredient and a pharmaceutically acceptable carbonic acid salt as an additive. The composition of the present invention is used for preparation of injectable solution which is of value for the treatment of diseases in animals including domestic fowls and human being, particularly for prevention or therapy of the infectious diseases caused by Gram-positive and Gram-negative bacteria in those animals or of value as an antiinfectious agent or a disinfectant, for example, for surgical instruments or hospital rooms. The compound "7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride" may be hereinafter abbreviated simply as "TTC".

TTC and its hydrates are new compounds which have strong antibacterial activity against Gram-positive and Gram-negative bacteria and is stable in storage. However, when TTC or its hydrate is intramuscularly injected, there are encountered the necrosis of muscle cells, discoloration or brown degeneration of the local tissue, hyperemia and other local reactions at the sites of injection. Thus, improvements have been needed in these aspects. Moreover, while TTC or its hydrate must be dissolved in a solvent such as distilled water before it may be administered through injection, it is rather slow to be dissolved, this being another disadvantage which has had to be overcome. The present invention did thorough analysis of the above problems and have now found that the antibacterial activity of TTC is not impaired in the presence of the pharmaceutically acceptable carbonic acid salt; that if a solvent such as distilled water is added to a mixture of TTC or its hydrate and a pharmaceutically acceptable carbonic acid salt, carbon dioxide gas is evolved and the dissolution of the medicament is considerably hastened by its agitating effect; and that the aforementioned local reactions are decreased where the solution thus obtained is administered through injection. The above findings were followed by further studies, on which basis this invention has been conceived and developed.

TTC or its hydrate, the starting material for the composition of this invention, can be easily produced, for example by reacting hydrogen chloride with 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid or the corresponding sodium salt, which acid and salt are described in Belgian Pat. No. 823861 and Dutch Pat. Application No. 7416609, in the presence or absence of water, recovering TTC or its hydrate from the reaction mixture after the reaction and, if desired, drying the product. The reaction may be effected in accordance with the salt formation reaction or the neutralization reaction between a base and an acid, the reaction having hitherto been well known among chemists in the field of cephalosporins. The reaction is usually carried out in a solvent or a mixture of solvents. The solvent may be the above-mentioned water, an organic solvent or a mixture thereof. The organic solvent is preferably acetone, ethanol, n-propanol, iso-propanol, methyl ethyl ketone, tetrahydrofuran, etc. The amount of hydrogen chloride to be reacted is usually 2 to 6 mols per mol of 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid and 3 to 7 moles per mol of the corresponding sodium salt. The reaction is normally carried out at temperature in the range of from −10° C. to 40° C. The reaction usually goes to completion within 5 hours. After the reaction, TTC or its hydrate is recovered from the reaction mixture by per se conventional procedure such as lyophilization or concentration of the reaction mixture, precipitation of TTC or its hydrate by the addition of less soluble solvent such as the above-mentioned organic solvent, etc.

When the reaction is carried out in a reaction system which does not contain water, thus obtained product is usually TTC (anhydrous). The anhydrous product may be converted into the corresponding hydrate of TTC. On the other hand, when the reaction is carried out in a reaction system containing water, the product is collected from the reaction mixture usually in the form of hydrate of TTC. The hydrate may be made into TTC for example by means of drying.

The cephalosporins (i.e. TTC and its hydrate) are shown by the formula:

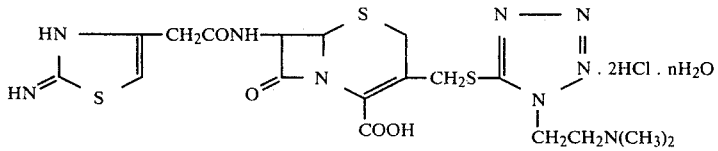

, in which n is a number in the range of 0≦n≦6, including anhydrate (n=0), monohydrate (n=1), dihydrate (n=2), trihydrate (n=3), tetrahydrate (n=4), pentahydrate (n=5) and hexahydrate (n=6) as well as compounds such that less than one mol of water is attached to any of said anhydrate and hydrates. The number n is preferably a number in the range of from one to four and the most preferably in the range of from one to two in view of stability. In this regard, it is to be understood that very small amount of organic solvent may be attached to TTC or its hydrate when organic solvent is used for the preparation of TTC or its hydrate as solvent, and it is to be construed that TTC or its hydrate having such small amount of organic solvent is covered by TTC or its hydrate throughout this specification and claims.

As examples of the pharmaceutically acceptable carbonic acid salt, there may be mentioned alkali metal hydrogen carbonates such as sodium hydrogen carbonate, potassium hydrogen carbonate, etc.; alkaline earth metal hydrogen carbonates such as magnecium hydrogen carbonate; alkali metal carbonates such as sodium carbonate, potassium carbonate, etc.; and alkaline earch metal carbonates such as magnesium carbonate, calcium carbonate, etc. The use of any of said alkali metal carbonates and alkali metal hydrogen carbonates has the advantage of a reduced pain of injection. The alkali metal hydrogen carbonates and alkaline earth metal hydrogen carbonates have the advantage that because they give rise to twice the volume of carbon dioxide gas as compared with alkali metal carbonates and alkaline earth metal carbonates when the composition of this invention is dissolved, the composition containing TTC or its hydrate is dissolved faster.

The antibiotic composition of this invention is produced by admixing TTC or its hydrate with a pharmaceutically acceptable carbonic acid salt by means which are conventional per se. In this admixing procedure, there may also be incorporated certain other known pharmaceutical additives including local anesthetics such as lidocaine hydrochloride, mepivacaine hydrochloride, etc. TTC or its hydrate, a pharmaceutically acceptable carbonic acid salt and other pharmaceutical additives are normally used in powdery or crystalline form and the composition of this invention is normally solid.

The proportion of TTC or it hydrate relative to a pharmaceutically acceptable carbonic acid salt is such that the ratio of hydrogen chloride as a moiety of TTC or its hydrate to the pharmaceutically acceptable carbonic acid salt is within the range of normally about 1:1 to 2 equivalents and preferably about 1:1 to 1.4 equivalents. It follows that the monoacidic base such as sodium hydrogen carbonate is normally used in a proportion of about 2 to 4 mols, preferably about 2 to 2.8 mols, per mol of TTC or its hydrate and that the diacidic base such as sodium carbonate is normally employed within the range of about 1 to 2 mols, preferably 1 to 1.4 mols, per mol of TTC or its hydrate.

The composition thus produced is usually aseptically packed into vials which are then vacuum-sealed and stored. By this procedure, not only is oxidative decomposition prevented but it is rendered easy to fill the vials with a solvent for the preparation of injections, at the time of use. As the solvent, e.g. distilled water, physiological saline or an aqueous solution of a local anesthetic, is infused into the vial, carbon dioxide gas is evolved to considerably hasten the dissolution of the medicament, quick dissolution being possible even under standing condition. Filling the plenum within the vial with carbon dioxide gas precludes oxidative decomposition, permitting us to store the TTC solution obtained in the form of a solution. The proportion of said solvent for dissolution is normally about 0.5 to 100 ml., preferably about 1 to 20 ml. per gram of TTC or its hydrate in terms of TTC.

Thus the present invention provides also vacuum-sealed vial in which the above-mentioned solid antibacterial composition containing TTC or its hydrate and a pharmaceutically acceptable carbonic acid salt is vacuum-seeled. It is preferable that volume of the vial satisfies the following equation:

$$V = \frac{P_1 V_0 + 6.236 \times 10^4 AT}{P_1 - P_2}$$

in which
  V is a vial volume in terms of ml.;
  $P_1$ is a pressure in the vial after filling the vial with the solvent in terms of mmHg;
  $P_2$ is a pressure in the vial before filling the vial with the solvent in terms of mmHg;
  A is molar amount of TTC or its hydrate in the vial;
  $V_0$ is volume of a solvent to be used for preparation of an injectable solution in terms of ml.; and
  T is an absolute temperature showing ambient temperature.

The pressure in the vial before filling the vial with the solvent represented by $P_2$ is usually the pressure of vacuum sealing, and it is normally in a range of from about 0 to 300 mmHg and preferably in the range of from about 0 to 100 mmHg.

The pressure in the vial after filling vial with the solvent represented by $P_1$ is usually in the range of from 600 to 1520 mmHg, preferably in the range of from 760 to 1140 mmHg.

The molar amount of TTC or its hydrate in the vial represented by A largely depends on the use of the resultant solution. For example, in case of injection for the therapy of infectious diseases caused by bacteria in man, it is usually in the range of from $1 \times 10^{-4}$ to $6 \times 10^{-3}$ mol.

The range and preferable ranges of the volume of the solvent, i.e. the ranges of $V_0$, are above mentioned.

In this regard, it should be understood that the aforementioned TTC solution may be obtained by adding a solution of the pharmaceutically acceptable carbonic acid salt in the aforementioned solvent to TTC or its hydrate, optionally incorporated with any one of other conventional pharmaceutical additives.

The TTC solution thus obtained may not only be used as external disinfectants or aseptics such as disinfectants for surgical instruments, hospital rooms, drinking water, etc. but also be intramuscularly or intravenously administered as drugs for the treatment of infectious diseases in warm-blooded animals including human beings, mice, rats and dogs as caused by Gram-positive bacteria (e.g. *Staphylococcus aureus*) or Gram-negative bacteria (e.g. *Escherichia coli, Krebsiella pneumoniae, Proteus vulgaris, Proteus morganii*).

For the purpose of using the composition as an external disinfectant for the disinfection of surgical instruments, there is prepared an aqueous solution of the composition containing 100 $\mu$/ml. of TTC, which may then be sprayed over the instruments. For the therapy of urinary tract infections in mice or human beings as caused by *Escherichia coli*, the TTC solution is intramuscularly or intravenously administered at the daily dose level of about 5 to 50 mg./kg. of TTC on an anhydrous TTC basis in three divided doses a day.

TTC or its hydrate may assume a couple of tautomeric forms by the tautomerization depicted below.

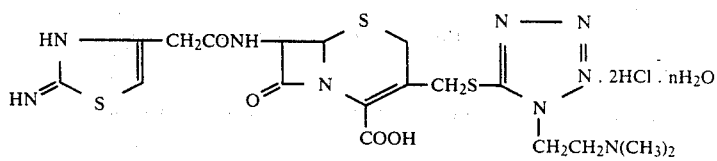

(Thiazoline Form)

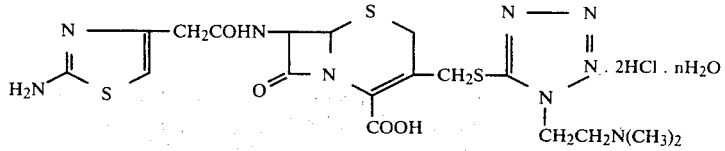

(Thiazole Form)

, in which n has the same meaning as defined above.

Much inquiry has heretofore been made into the modes of existence of compounds of this type and the literature refers to the thiazoline form under certain conditions [Acta Crystallographica 27, 326 (1971] and the thiazole form under other conditions [Chemistry and Industry, 1966 ed., p. 1634]. However, various determinations have shown that TTC or its hydrate seems to predominantly assume the thiazoline form, because this form is stabilized by a contributory effect of hydrogen bonding as shown by the following formula.

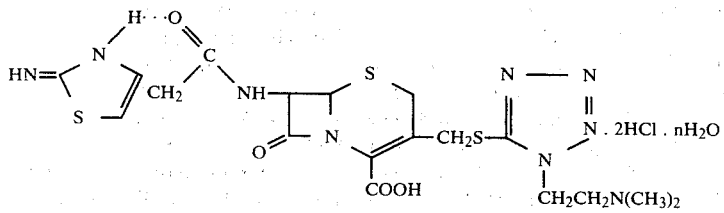

in which n has the same meaning as defined above. However, this kind of equilibrium is liable to shift rather easily under the influence of various factors, e.g. the pH and polarity of the solvent used, temperature, etc., to which TTC or its hydrate may be subjected. Thus, TTC or its hydrate may be designated in accordance with whichever of the two forms. In this specification and the claims appended thereto, however, TTC and its hydrate are designated by their thiazoline forms. However, TTC and its hydrate in this invention should be construed to cover all the above tautomers.

Throughout the specification, "minimum inhibitory concentration", "gram(s)", "kilogram(s)", "liter(s)", "milligram(s)", "milliliter(s)", "percent", "Karl Fischer's method", "infrared", "nuclear magnetic resonance", "minute(s)", "calculated", "centimeter(s)", "microgram(s)", "singlet", "broad singlet", "doublet", "triplet" and "double doublet" may be abbreviated as "M.I.C.", "g.", "kg.","l.", "mg.", "ml.", "%", "K.F. method", "I.R.", "N.M.R.", "min.", "calcd.", "cm.", "mcg.", "s", "bs", "d", "t" and "dd", respectively.

Reference Example 1

The antibacterial potency (M.I.C.) and toxicity of TTC (1) Antibacterial spectrum (agar dilution)
Staphylococcus aureus FDA 209 P: 0.39 mcg./ml.
Staphylococcus aureus 1840: 0.78 mcg./ml.
Escherichia coli NIHJ JC-2: 0.2 mcg./ml.
Escherichia coli O-111: 0.05 mcg./ml.
Escherichia coli T-7: 1.56 mcg./ml.
Krebsiella pneumoniae DT: 0.1 mcg./ml.
Proteus vulgaris IFO 3988: 1.56 mcg./ml.
Proteus morganii IFO 3848: 0.39 mcg./ml.

(2) Acute toxicity (mouse, intraperitoneal)
$LD_{50} \geq 20$ g./kg.

The acute toxicity data is for a 1:1 (molar) mixture of TTC and sodium carbonate.

Reference Example 2

(1) To 400 g. of 2-(N,N-dimethylamino)ethylamine was added 2.4 l. diethyl ether and after cooling, a mixture of 400 g. of carbon disulfide and 4.0 l. of diethyl ether was added dropwise at 18° to 23° C. over a period of 1 hour. The mixture was stirred at that temperature for another hour, after which the resultant crystals of 2-(N,N-dimethylamino)-ethylaminecarbodithioic acid were recovered by filtration. Yield 695 g., yield 93.3%, m.p. 156° to 157° C.

To the crystals thus obtained above was added 4.4 l. of water and with stirring, 4.32 l. of 1 N-KOH was added dropwise at 8° to 13° C. over a period of 30 to 40 min., further followed by the dropwise addition of a mixture of 668 g. of methyl iodide and 6.68 l. of acetone at 0° to 5° C. over a period of 30 to 40 min. The mixture was stirred at a temperature of the same range for another 30 min. The acetone was distilled off under reduced pressure and the water layer was extracted with 3 l. of ethyl acetate and, then, 2 l. of the same solvent. The ethyl acetate layer was washed with 2 l. of a saturated aqueous solution of sodium chloride, dried over sodium sulfate and concentrated. The resultant crystals were recrystallized by the addition of 500 ml. of n-hexane. By the above procedure was obtained 575 g. of S-methyl-[2-(N,N-dimethylamino)]ethylamine carbodithioate, m.p. 61° to 62° C., in a yield of 75.5%. To 520 g. of the above crystals was added 1.05 l. of ethanol together with 190 g. of sodium azide and 2.1 l of pure water, and the mixture was heated under reflux for 3 hours, followed by the addition of a solution of 52 g. crystals of S-methyl-[2-(N,N-dimethylamino)]ethylamine carbodithioate in 100 ml. ethanol. The mixture was refluxed for 1 hour and, then, cooled to 20° C. To this was added 2.0 l. of pure water and, in nitrogen streams, the mixture was adjusted to pH 2 to 2.5 with concentrated hydrochloric acid. The ethanol was distilled off under reduced pressure and the residue was adsorbed on Amberlite IR-120 (H type) manufactured by Rohm and Haas Co., which was washed with pure water until acidity disappeared. The eluate obtained with 5% (weight/weight) aqueous ammonia was concentrated to obtain 350 g. crystals of 1-[2-(N,N-dimethylamino)ethyl]-5-mercapto-1H-tetrazole, m.p. 218° to 219° C., in a yield of 69.3%, N.M.R. (D₂O, with an equimolar amount of NaHCO₃ added, τ value):

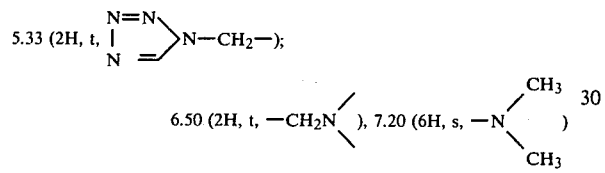

(2) To 2.6 l. of water was added 206 g. of 7β-[2-(2-imino-4-thiazolin-4-yl)acetamido]-3-acetyloxymethyl-3-cephem-4-carboxylic acid. Then, under stirring, 86.5 g. of 1-[2-(N,N-dimethylamino)ethyl]-5-mercapto-1H-tetrazole obtained in the above (1) and 42 g. of sodium hydrogen carbonate were added. The mixture was stirred at 65° C. for 75 min. and, then, cooled to 10° C. Following addition of 250 ml. of 5 N-HCl to adjust the mixture pH 2.0, the insolubles were recovered by filtration and rinsed with water. The filtrate and washings were combined, adjusted to pH 5.2 by the addition of sodium hydrogen carbonate and adsorbed on a column of 10 l. Amberlite XAD-II (100-200 mesh). The column was washed with 60 l. of water and, then, elution was carried out with 20% aqueous methanol and, then, 40% aqueous methanol. The fractions (11 l.) containing the desired compound were concentrated to 5 l. and passed columnwise over 300 g. of activated alumina (about 300 mesh) manufactured by Wako Pure Chemical Industries, Ltd. in Japan and over 100 ml. of Amberlite IR-120 (H type). The column was washed with water and the effluent and washings were pooled and concentrated to 2 l. The concentrate was cooled to 5° C. and stirred with 5 g. of activated carbon for 5 min. The activated carbon was filtered off and the filtrate was lyophilized to obtain 51.2 g. of 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid.

N.M.R. (60 MHz D₂O, τ value):

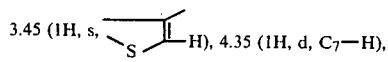 H), 4.35 (1H, d, C₇—H),

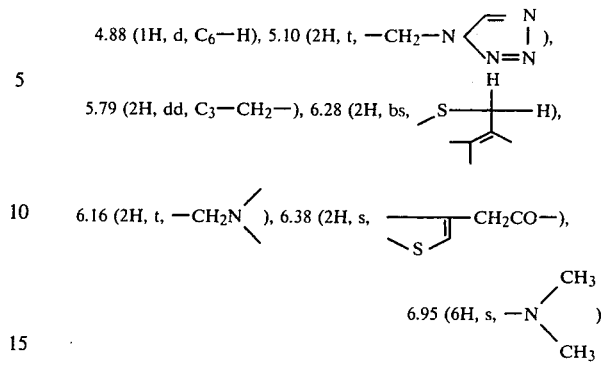

(3) 0.5 l. of an aqueous solution containing 51.0 g. of 7β-[2-(2-imino-4-thiazolin-4-yl)acetamido]-3-{1-[2-(N,N-dimethylamino)ethyl]-1H-tetrazol-5-yl)thiomethyl-3-cephem-4-carboxylic acid obtained in above (2) was acidified to pH 2.0 with 12 N-HCl and cooled to 10° C. and stirred with 0.7 g. of activated carbon for 5 min. The activated carbon was filtered off and washed with 50 ml. of water. The filtrate and washings were combined and concentrated under reduced pressure to 228 ml. at an internal temperature of 15° to 17° C. The concentrate was filtered and insolubles filtered off were washed with water. The filtrate and washings were combined to obtain 238 ml. solution which contained 47.8 g. of the above carboxylic acid. To the solution was added 0.02 l. of acetone, followed by addition of 17.0 ml. of 12 N-HCl. Then, 0.7 l. of acetone was added over a period of 10 min. and, at 5° to 10° C., the mixture was stirred for 2 hours. Then, 0.7 l. of acetone was further added over a period of 30 min. The mixture was further stirred for 1 hour and allowed to stand overnight. The resultant crystals were recovered by filtration and washed with 100 ml. ×4 of acetone. The crystals were spread in a dish and allowed to dry in the air to remove most of the acetone. The crystals were then dried under reduced pressure (45 mmHg) for 1 hour. The crystals at this stage were composed of 77.7% of the above carboxylic acid, 10.8% of hydrogen chloride, 9.24% of water and 2.2% of acetone. The crystals were packed into a glass filter and pre-moistened nitrogen gas was passed through the bed of crystals for 4 hours to completely remove the acetone. The water content of the crystals at this stage was 16.4% (K.F. method). The crystals were further dried under reduced pressure (45 mmHg) to obtain 52.5 g. crystals of 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride hydrate. The physical properties of this crystalline product were as follows. Water content (K.F. method) 3.12%; Purity on an anhydrate basis 99.5%; Crystalline, based on its powder X-ray diffraction pattern.

Examination of the product under a polarizing microscope revealed that it was crystalline.

Elemental analysis, $C_{18}H_{23}N_9S_3O_4 \cdot 2HCl \cdot H_2O$: Found C, 34.78; H, 4.51; N, 20.62; S, 15.31; Cl, 11.77. Calcd. C, 35.06; H, 4.41; N, 20.45; S, 15.60; Cl, 11.50.

Reference Example 3

(1) 5.0 l. of an aqueous solution containing 510 g. of 7β-[2-(2-imino-4-thiazolin-4-yl)acetamido]-3-{1-[2-(N,N-dimethylamino)ethyl}-1H-tetrazol-5-yl]thiomethyl-3-cephem-4-carboxylic acid obtained in Reference Example 2 (2) was acidified to pH 2.0 with 12 N-HCl and cooled to 1° C. and stirred with 7.0 g. of activated carbon for 5 min. The activated carbon was removed by filtration and rinsed with 500 ml. of water. The filtrate and washings were combined and concentrated under reduced pressure to 2.28 l. at an internal temperature of 15° to 17° C. The concentrate was filtered and washed again with water. The filtrate and washings, which totalled 2.38 l., contained 470 g. of the above carboxylic acid. To the filtrate was added 200 ml. of acetone, followed by addition of 170 ml. of 12 N-HCl. Then, 7 l. of acetone was further added over a period of 10 min. and the mixture was stirred at 5° to 10° C. for 2 hours. Thereafter, 7 l. of acetone was further added over a period of 30 min. The mixture was stirred for 1 hour and, then, allowed to stand overnight. The resultant crystals were collected by filtration and washed with 1 l.×4 of acetone. (A sample of the crystals was taken and dried in a desiccator at room temperature at 30 mmHg for 30 min. The water content as determined by K.F. method was 8.9%, with 2.2% of acetone attached. The water content calculated for $C_{18}H_{23}N_9O_4S_3.2HCl.3H_2O$ was 8.28%). The above crystals were transferred to a separate glass filter and nitrogen gas pre-moistened by passage through a water-containing scrubbing bottle (The water temperature was held at 25° to 30° C.) was passed through the bed of crystals at a rate of 8 l./min. for 6 hours. (A sample of the crystals thus obtained was separated and investigated for water content by K.F. method. The water content was 19.5%. The water content as calculated for $C_{18}H_{23}N_9O_4S_3.2HCl.8H_2O$ was 19.41%. This product contained no acetone at all and its powder X-ray diffraction pattern showed that it was crystalline). The above crystals were spread in a layer about 3 cm thick and dried at 30° C. at 5 mmHg for 1.5 hours. (The water content of a sample of these crystals was 17.2% as determined by K.F. method. The water content calculated for $C_{18}H_{23}N_9O_4S_3.2HCl.7H_2O$ was 17.41%). The above crystals were further dried under the same conditions for 1.5 hours, the water content as determined by K.F. method being 15.4%. (The water content calculated for $C_{18}H_{23}N_9O_4S_3.2HCl.6H_2O$ was 15.3% water). The crystals were further dried for 1.5 hours, the K.F. method water content being 13.3%. (The water content calculated for $C_{18}H_{23}N_9O_4S_3.2HCl.5H_2O$ was 13.08%). The above crystals were further dried for 1.5 hours, the K.F. method water content being 10.5%. (The calculated water content based on $C_{18}H_{23}N_9O_4S_3.2HCl.4H_2O$ was 10.75%). After drying for another 1.5 hours, 525 g. of crystals were obtained.

Water content (K.F. method) 8.50% (calcd. for $C_{18}H_{23}N_9O_4S_3.2HCl.3H_2O=8.28\%$); powder X-ray diffraction pattern: crystalline; Cl content (AgNO₃ method) 10.6% (calcd. for $C_{18}H_{23}N_9O_4S_3.2HCl.3H_2O=10.8\%$).

(2) The crystals obtained in (1) above were dried at 30° C., at 2 mmHg and in the presence of phosphoric anhydride, for 5 hours, whereby 510 g. of crystals were obtained.

Water content (K.F. method) 5.7% (calcd. for $C_{18}H_{23}N_9O_4S_3.2HCl.2H_2O=5.68\%$); powder X-ray diffraction pattern: crystalline. I.R.(KBr)cm⁻¹: 1770(β-lactam), Sharp peaks characteristic of crystals appear at 1670, 1190(sh.) and 1170.

(3) The crystals obtained in (2) were dried at 30° C., at 2 mmHg and in the presence of phosphoric anhydride for 8 hours. By the above procedure was obtained 495 g. of crystals.

Water content (K.F. method) 3.12% (calcd. for $C_{18}H_{23}N_9O_4S_3.2HCl.H_2O=2.92\%$); purity on anhydrate basis (high-speed liquid chromatography, on dichloride anhydrate basis) 99.5%; powder X-ray diffraction pattern: crystalline;

Elemental analysis, for $C_{18}H_{23}N_9O_4S_3.2HCl.H_2O$: Found C, 34.78; H, 4.51; N, 20.62; S, 15.31; Cl, 11.77. Calcd. C, 35.06; H, 4.41; N, 20.45; S, 15.60; Cl, 11.50.

$[\alpha]_D^{20}(c=1\%, H_2O)=+67.0°$; residual solvent (acetone) 50 ppm. or less; Cl content (AgNO₃) 11.4%; calcd. 11.50%; λmax (H₂O) 258 mμ(ε19,500).

(4) 3 g. of the crystals obtained in (3) were dried at 5 mmHg and in the presence of phosphoric anhydride for 2 hours at 20° C. and 5 hours at 50° C., whereupon 2.6 g. of powdery product was obtained.

Water content (K.F. method) 0.3% (calcd. for $C_{18}H_{23}N_9O_4S_3.2HCl.0.1H_2O=0.3\%$); powder X-ray pattern: amorphous; polarizing microscopy: crossed Nicol's prisms, interference colors on rotation of the slide, indicating optical anisotropy; Purity 99.6% (high-speed liquid chromatography, on a dihydrochloride anhydrate basis)

REFERENCE EXAMPLE 4

1.72 g. of 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid obtained in Reference Example 2 (2) was suspended in 10 ml. of anhydrous methanol. To the suspension was added 6.20 ml. of N-hydrogen chloride anhydrous methanol solution, and the mixture was stirred to obtain a solution. The solution is portionwise added to 150 ml. of anhydrous ether to form precipitates.

The precipitates were collected by filtration, washed with anhydrous ether and dried under reduced pressure to obtain anhydrous 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride (i.e. TTC).

Elemental analysis as $C_{18}H_{23}N_9O_4S_3.2HCl$: Found C, 36.31; H, 4.26; N, 20.61. Calcd. C, 36.12; H, 4.21; N, 21.06.

EXAMPLE 1

250 g. of TTC hydrate as produced according to Reference Example 2 (3) was aseptically admixed with 44.3 g. of sterile particles-free sodium carbonate and the aseptic mixture was packed in portions of 250 mg. in terms of TTC into sterilized dry vials of 12 ml. capacity which were vacuum-sealed at 50 mmHg. The contents are dissolved quite readily upon addition of 3 ml. of distilled water.

EXAMPLE 2

By the same procedure as Example 1, 500 g. of TTC hydrate produced in Reference Example 3 (2) was mixed with 115.2 g. of potassium carbonate and the mixture was packed in portions of 500 mg. in terms of TTC into sterilized dry vials of 17 ml. capacity. The vials were vacuum-sealed at 50 mmHg.

EXAMPLE 3

250 g. of TTC hydrate as produced according to Reference Example 2 (3) was aseptically mixed with 70.2 g. of sterile particles-free sodium hydrogen carbonate and the mixture was packed into sterilized dry vials of 17 ml. capacity in portions of 250 mg. based on the weight of TTC. The vials were vacuum-sealed in a vacuum of 2 mmHg.

EXAMPLE 4

250 g. of TTC hydrate produced in Reference Example 3 (3) was aseptically mixed with 35.2 g. of sterile particles-free magnesium carbonate and 125 mg. portions of the mixture in terms of TTC were respectively packed into sterilized dry vials of 9 ml. capacity. The vials were vacuum-sealed in a vacuum of 20 mmHg.

EXAMPLE 5

The procedure of Example 4 was repeated except that 83.6 g. of calcium carbonate was used in lieu of 35.2 g. of magnesium carbonate. By this procedure was obtained an antibiotic composition.

EXAMPLE 6

The procedure of Example 3 was repeated except that 250 g. of TTC hydrate prepared in Reference Example 4 were used in lieu of 250 g. of TTC hydrate produced in Reference Example 2 (3). By this procedure was obtained vacuum-sealed vials containing an antibiotic composition.

EXAMPLE 7

The procedure of Example 1 was repeated except that 250 g. of any one of the TTC produced in Reference Example 4 and the TTC hydrates produced in Reference Example 3 (2) and 3 (4) was used in lieu of 250 g. TTC hydrate produced in Reference Example 2 (3).

Experiment 1

The solution produced according to Example 1 was subcutaneously administered to mice infected with the following pathogenic microorganisms to ascertain the $ED_{50}$ values (mg. of TTC/kg. of mouse).

$ED_{50}$ values

*Staphylococcus aureus:*
308 A-1
7.14 (mg./kg.)
*Escherichia coli:*
0-111
0.074 (mg./kg.)
*Proteus vulgaris:* IFO-3988
1.32 (mg./kg.)

Experiment 2

250 mg. of TTC hydrate obtained in Reference Example 2 (3) was admixed with 50 mg. of sodium carbonate and the mixture was packed into a vial of 12 ml. capacity which was then vacuum-sealed in a vacuum of 50 mmHg. The product was designated Sample A. On the other hand, a mixture of 250 mg. of TTC hydrate obtained in Reference Example 2 (3) and 50 mg. of sodium carbonate was packed into a vial of 12 ml. capacity. This vial was not vacuum-sealed and designated Sample B. 250 mg of TTC hydrate obtained in Reference Example 2 (3) alone was filled into a 12 ml. vial, which was not vacuum-sealed and designated Sample C. To each of the Samples was added 3 ml. of distilled water and the times of dissolution were measured. The colors of the Samples 3 hours after dissolution were also evaluated.

| Sample | Dissolution time | Color 3 hours after dissolution |
|---|---|---|
| A | 15 sec. | Yellow to yellowish tan |
| B | 70 sec. | Yellow to yellowish tan |
| C | 180 sec. | Reddish yellow |

Provided that, in dissolution, Samples A and B were allowed to stand, while Sample C was shaken vigorously.

EXPERIMENT 3

1 ml. portions of each of the following injectable fluids were injected into the vastus lateralis muscles of rabbits and, after 24 hours, the animals were killed. The muscles were taken and dissected to examine the degrees of injury (local reactions) by the naked eye. The findings were scored according to the following scheme.

| Score | Symptom |
|---|---|
| 0 | No discernible gross reaction |
| 1 | Slight hyperemia |
| 2 | hyperemia and moderate discoloration |
| 3 | Discoloration |
| 4 | Brown degeneration or necrosis with hyperemia |
| 5 | Widespread necrosis |

The results are set forth below:

| Composition | Local reaction Single administration, after a day |
|---|---|
| TTC hydrate 250 mg.* | 4 |
| TTC hydrate 250 mg.* + anhydrous sodium carbonate 50 mg. | 0 |
| TTC hydrate 250 mg.* + sodium hydrogen carbonate 86 mg. | 0 |

*TTC hydrate used in the above compositions were obtained in Reference Example 2 (3).

The powders of each composition were respectively dissolved in 2 ml. of distilled water and the local reactions were investigated.

What is claimed is:

1. A vacuum-sealed vial, which contains a solid antibiotic composition comprising 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride or its hydrate and sodium carbonate or sodium hydrogen carbonate, the ratio of the hydrogen chloride moiety of 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride or its hydrate relative to said sodium carbonate or sodium hydrogen carbonate being substantially 1:1 to 2 equivalents, the pressure in the vial being in the range of from 0 to 300 mmHg.

2. A vacuum-sealed vial as claimed in claim 1, wherein sodium carbonate is contained in the composition.

3. A vacuum-sealed vial as claimed in claim 1, wherein sodium hydrogen carbonate is contained in the composition.

4. A vacuum-sealed vial as claimed in claim 1, wherein 7β-[2-(2-imino-4-thiazolin-4-yl)acetamido]-3-{1-[2-(N,N-dimethylamino)-ethyl]-1H-tetrazol-5-yl}thiomethyl-3-cephem-4-carboxylic acid dihydrochloride hydrate, of which the water content is substantially 1 to 4 mols per mol of 7β-[2-(2-imino-4-thiazolin-4-yl)acetamido]-3-}1-[2-(N,N-dimethylamino)ethyl]-1H-tetrazol-5-yl}thiomethyl-3-cephem-4-carboxylic acid dihydrochloride moiety, is contained in the composition.

5. A vacuum-sealed vial as claimed in claim 4, wherein the water content is substantially 1 to 2 mols per mol of β7-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride moiety.

6. A vacuum-sealed vial, which contains a solid antibiotic composition comprising 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride hydrate, of which the water content is substantially 1 to 4 mols per mol of 7β-[2-(2-imino-4-thiazolin-4-yl)acetamido]-3-{1-[2-(N,N-dimethylamino)ethyl]-1H-tetrazol-5-yl}-thiomethyl-3-cephem-4-carboxylic acid dihydrochloride moiety, and sodium carbonate, the amount of sodium carbonate being substantially 1 to 2 mols per mol of said hydrate, the pressure in the vial being in the range of from 0 to 300 mmHg.

7. A vacuum-sealed vial as claimed in claim 6, wherein the water content is substantially 1 to 2 mols per mol of 7β-[2-(2-imino-4-thiazolin-4-yl)acetamido]-3-{1-[2-(N,N-dimethylamino)ethyl]-1H-tetrazol-5-yl}thiomethyl-3-cephem-4-carboxylic acid dihydrochloride moiety.

* * * * *

UNITED STATES PATENT AND TRADEMARK OFFICE
CERTIFICATE OF CORRECTION

PATENT NO. : 4,241,057
DATED : December 23, 1980
INVENTOR(S) : Kenzo Ishizuka, Hiroshi Fujisawa et al.

It is certified that error appears in the above—identified patent and that said Letters Patent is hereby corrected as shown below:

On the title page Insert:

-- (30) Foreign Application Priority Data
    August 31, 1976    Japan    51-104582 --.

Signed and Sealed this

Eleventh Day of May 1982

[SEAL]

Attest:

GERALD J. MOSSINGHOFF

*Attesting Officer*    *Commissioner of Patents and Trademarks*

UNITED STATES PATENT AND TRADEMARK OFFICE

CERTIFICATE EXTENDING PATENT TERM
UNDER 35 U.S.C. 156

Patent No.     : 4,241,057

Dated          : December 23, 1980

Inventor(s)    : KENZO ISHIZUKA ET AL

Patent Owner   : TAKEDA CHEMICAL INDUSTRIES, LTD.

This is to certify that there has been presented to the

COMMISSIONER OF PATENTS AND TRADEMARKS an application under 35 U.S.C. 156 for an extension of the
patent term. Since it appears that the requirements of the law
have been met, this certificate extends the term of the patent
for the period of

2 YEARS with all rights pertaining thereto as provided by 35
USC 156 (b).

I have caused the seal of the Patent
and Trademark Office to be affixed
this 11th day of December 1989.

Jeffrey M. Samuels
Acting Commissioner of
   Patents and Trademarks